(12) United States Patent
Avila et al.

(10) Patent No.: US 12,171,479 B2
(45) Date of Patent: *Dec. 24, 2024

(54) ELECTROSURGERY PATIENT PAD MONITOR

(71) Applicant: CooperSurgical, Inc., Trumbull, CT (US)

(72) Inventors: Alberto Avila, Trumbull, CT (US); John Glaberson, Sandy Hook, CT (US)

(73) Assignee: CooperSurgical, Inc., Trumbull, CT (US)

( * ) Notice: Subject to any disclaimer, the term of this patent is extended or adjusted under 35 U.S.C. 154(b) by 385 days.

This patent is subject to a terminal disclaimer.

(21) Appl. No.: 17/841,922

(22) Filed: Jun. 16, 2022

(65) Prior Publication Data

US 2022/0378492 A1 Dec. 1, 2022

Related U.S. Application Data

(63) Continuation of application No. 16/412,615, filed on May 15, 2019, now Pat. No. 11,376,060.

(51) Int. Cl.
*A61B 18/22* (2006.01)
*A61B 18/12* (2006.01)
(Continued)

(52) U.S. Cl.
CPC .......... *A61B 18/1233* (2013.01); *A61B 18/16* (2013.01); *G16H 40/63* (2018.01);
(Continued)

(58) Field of Classification Search
CPC . A61B 18/1206; A61B 18/1233; A61B 18/14; A61B 18/16; A61B 2018/00666;
(Continued)

(56) References Cited

U.S. PATENT DOCUMENTS 5,496,313 A 3/1996 Gentelia et al.
5,817,093 A 10/1998 Williamson et al.
(Continued)

FOREIGN PATENT DOCUMENTS

CN 206587032 10/2017
CN 207136905 3/2018
(Continued)

OTHER PUBLICATIONS

International Preliminary Report on Patentability for International Application No. PCT/US2020/032709 dated Nov. 25, 2021.
(Continued)

*Primary Examiner* — Tigist S Demie
(74) *Attorney, Agent, or Firm* — Fish & Richardson P.C.

(57) ABSTRACT

An electrosurgery system includes a first generator configured to output an operating signal. The system also includes a pathway for the operating signal, the pathway includes an active electrode and a patient pad. The system also includes a circuit configured to measure a complex impedance of the patient pad. The circuit includes a second generator configured to output a measuring signal. The system also includes a voltage transformer, a current transformer, and a plurality of filters.

20 Claims, 7 Drawing Sheets

(51) Int. Cl.
 *A61B 18/16* (2006.01)
 *G16H 40/63* (2018.01)
 *A61B 18/00* (2006.01)
 *A61B 18/14* (2006.01)

(52) U.S. Cl.
 CPC ............... *A61B 2018/00666* (2013.01); *A61B 2018/00827* (2013.01); *A61B 2018/00875* (2013.01); *A61B 2018/00892* (2013.01); *A61B 18/1206* (2013.01); *A61B 2018/1273* (2013.01); *A61B 18/14* (2013.01)

(58) Field of Classification Search
 CPC ........... A61B 2018/00827; A61B 2018/00875; A61B 2018/00892; A61B 2018/1273; A61B 2018/1286
 See application file for complete search history.

(56) References Cited

U.S. PATENT DOCUMENTS

| | | | |
|---|---|---|---|
| 6,063,075 A | 5/2000 | Mihori | |
| 6,229,725 B1 | 5/2001 | Nielsen | |
| 2005/0021022 A1 | 1/2005 | Sturm et al. | |
| 2010/0121318 A1 | 5/2010 | Hancock et al. | |
| 2011/0077641 A1 | 3/2011 | Dunning | |
| 2011/0172660 A1 | 7/2011 | Bales, Jr. et al. | |
| 2013/0066220 A1 | 3/2013 | Weinkam et al. | |
| 2017/0135744 A1* | 5/2017 | Smith | A61B 18/1233 |
| 2020/0360074 A1 | 11/2020 | Avila et al. | |

FOREIGN PATENT DOCUMENTS

| | | |
|---|---|---|
| DE | 102017210246 | 1/2018 |
| EP | 1 157 666 | 11/2001 |
| JP | H8503381 | 4/1996 |
| JP | H8229050 | 9/1996 |
| JP | 6636368 | 1/2020 |
| WO | WO 93/08755 | 5/1993 |
| WO | WO 2018/222899 | 12/2018 |

OTHER PUBLICATIONS

International Search Report and Written Opinion of the International Searching Authority for International Application No. PCT/US2020/032709, dated Aug. 21, 2020.

* cited by examiner

ELECTROSURGERY PATIENT PAD MONITOR

CROSS REFERENCE TO RELATED APPLICATIONS

This application is a continuation of and claims priority under 35 U.S.C. § 120 from U.S. application Ser. No. 16/412,615, filed on May 15, 2019, the contents of which is incorporated herein by reference in its entirety.

BACKGROUND

This description relates to electrosurgery systems, which are employed across a wide breadth of surgical disciplines.

In electrosurgery, a high-frequency (e.g., a radio frequency) alternating polarity, electrical current is applied to biological tissues for the purposes of cutting, coagulating, desiccating, or fulgurating, etc. the biological tissue. In an electrosurgery system, the electrical current is generated by a high frequency (HF) generator, connected to an instrument with one (monopolar) or two (bipolar) electrodes. In a configuration involving a monopolar instrument, an active electrode of the instrument is energized for surgical operation and a dispersive electrode, located at another location on the patient's body, disperses the electrical current to prevent thermal injury to the underlying tissue. Due to the potentially dangerous levels of electrical current generated by the HF generator, electrical characteristics of the electrosurgery system are monitored, such as the impedance of components associated with the dispersive electrode of the system (e.g., a patient pad).

SUMMARY

The systems and techniques described can improve the safety of electrosurgery systems by providing an accurate and reliable measurement of electrical characteristics of the electrosurgery systems, such as the impedance of a patient pad, over a broad range of resistances (e.g., 0Ω-1,000Ω or 0Ω-10,000Ω). In addition, the systems and techniques described can limit the presence of beat frequencies resulting from the interference between a monitoring signal and a signal generated by the HF generator of the electrosurgery system. For example, by measuring the impedance of the patient pad, a surgical operator or lab technician can ensure that a consistent and direct connection is maintained between a patient and the dispersive electrode of the electrosurgery system, thus decreasing the risk of thermal injury.

In one aspect, an electrosurgery system includes a first generator configured to output an operating signal. The system also includes a pathway for the operating signal, the pathway includes an active electrode and a patient pad. The system also includes a circuit configured to measure a complex impedance of the patient pad. The circuit includes a second generator configured to output a measuring signal. The system also includes a voltage transformer, a current transformer, and a plurality of filters.

Implementations may include one or more of the following features. The voltage transformer may be a resonant transformer. The voltage transformer has one primary and two secondaries, or, a single center-tapped secondary. The voltage transformer may have a Q factor in the range of 3 to 40. The current transformer may have two primaries and one secondary. The secondary of the current transformer may be configured to measure the sum of a first current corresponding to the first primary of the current transformer and a second current corresponding to the second primary of the current transformer. The complex impedance may be provided by a load and ranges from 0 to 10,000 ohms. A frequency of the measuring signal may be fixed. The frequency of the measuring signal may be selected to prevent beat frequencies resulting from interference with the operating signal. The frequency of the measuring signal may be selected to be within the range of 136 kHz to 138 kHz. The operating signal may have a frequency within the range of 494 kHz to 496 kHz. The circuit may include (i) a voltage channel configured to measure a complex excitation voltage associated with the voltage transformer, and, (ii) a current channel configured to measure a complex induced current associated with the current transformer. The complex impedance may be calculated by dividing the complex excitation voltage by the complex induced current.

In another aspect, a method for monitoring the complex impedance of a patient pad includes generating an operating signal by a first generator of an electrosurgery system. The operating signal is configured to travel along a pathway comprising an active electrode and a patient pad. The method also includes generating a measuring signal by a second generator. The second generator being part of a circuit that further includes a voltage transformer, a current transformer, and a plurality of filters. The method also includes measuring a complex excitation voltage by a voltage channel associated with the voltage transformer. The method also includes measuring a complex induced current by a current channel associated with the current transformer, and, dividing the complex excitation voltage by the complex induced current to calculate a complex impedance value.

Implementations may include one or more of the following features. The method may further include comparing the complex impedance value to a threshold resistance value. The voltage transformer may be a resonant transformer. The voltage transformer may have one primary and two secondaries, or, a single center-tapped secondary. The voltage transformer may have a Q factor in the range of 3 to 40. The current transformer may have two primaries and one secondary. The secondary of the current transformer may be configured to measure the sum of a first current corresponding to the first primary of the current transformer and a second current corresponding to the second primary of the current transformer. The complex impedance may be provided by a load and ranges from 0 to 10,000 ohms. A frequency of the measuring signal may be fixed. The frequency of the measuring signal may be selected to prevent beat frequencies resulting from interference with the operating signal. The frequency of the measuring signal may be selected to be within the range of 136 kHz to 138 kHz. The operating signal may have a frequency within the range of 494 kHz to 496 kHz. The voltage channel may include a first set of bandpass filters, a first synchronous demodulator, and a first set of low pass filters. The current channel may include a second set of bandpass filters, a second synchronous demodulator, and a second set of low pass filters. The first synchronous demodulator may be configured to sequentially receive a first reference signal and a second reference signal, a 90 degree phase difference may be experienced by the first synchronous demodulator when the second reference signal is received relative to a phase difference experienced by the first synchronous demodulator when the first reference signal is received. An open circuit, fixed resistance, and short circuit conditions may be used for self-calibration.

These and other aspects, features, and various combinations may be expressed as methods, apparatus, systems, means for performing functions, program products, etc.

Other features and advantages will be apparent from the description and the claims.

DETAILED DESCRIPTION

Figure 1A:
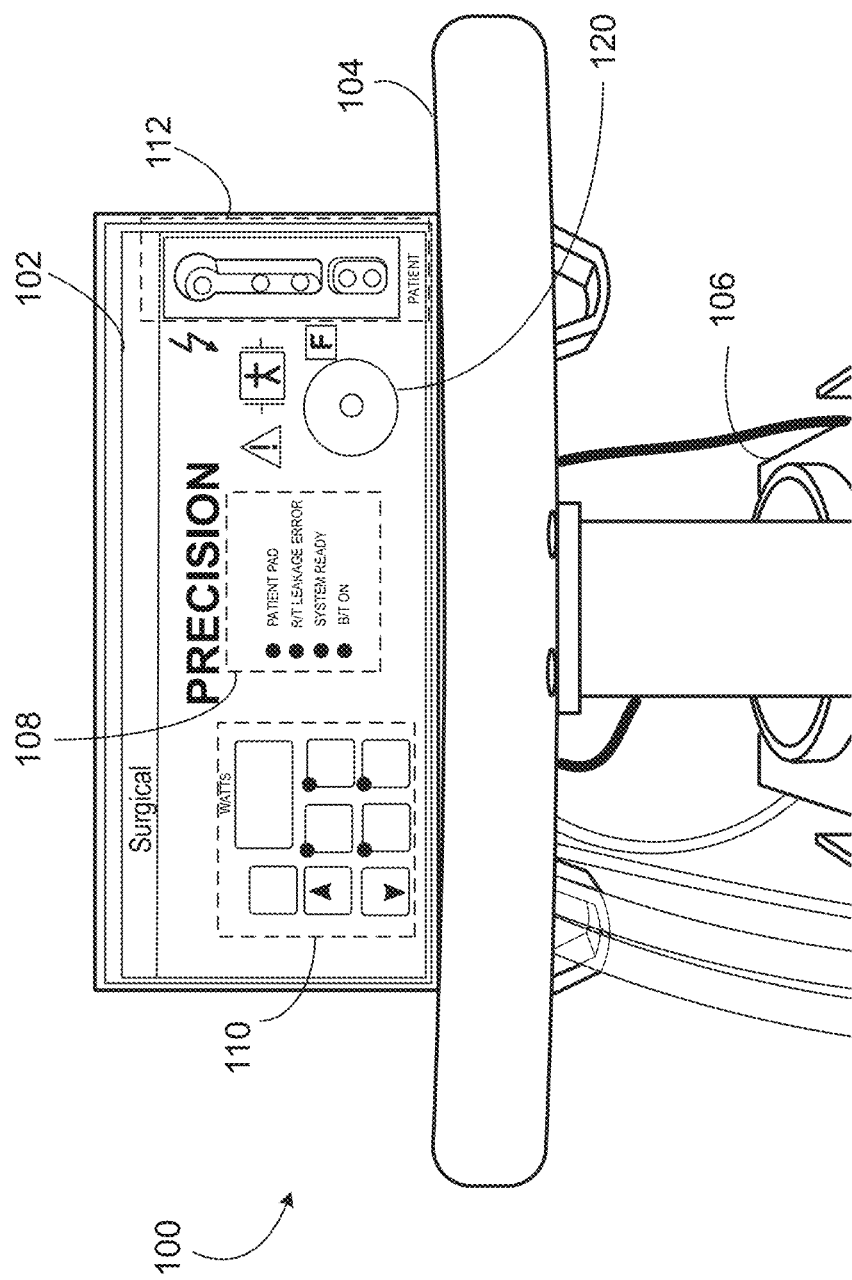
FIG. 1A is an illustration of an electrosurgery system.
Figure 1B:
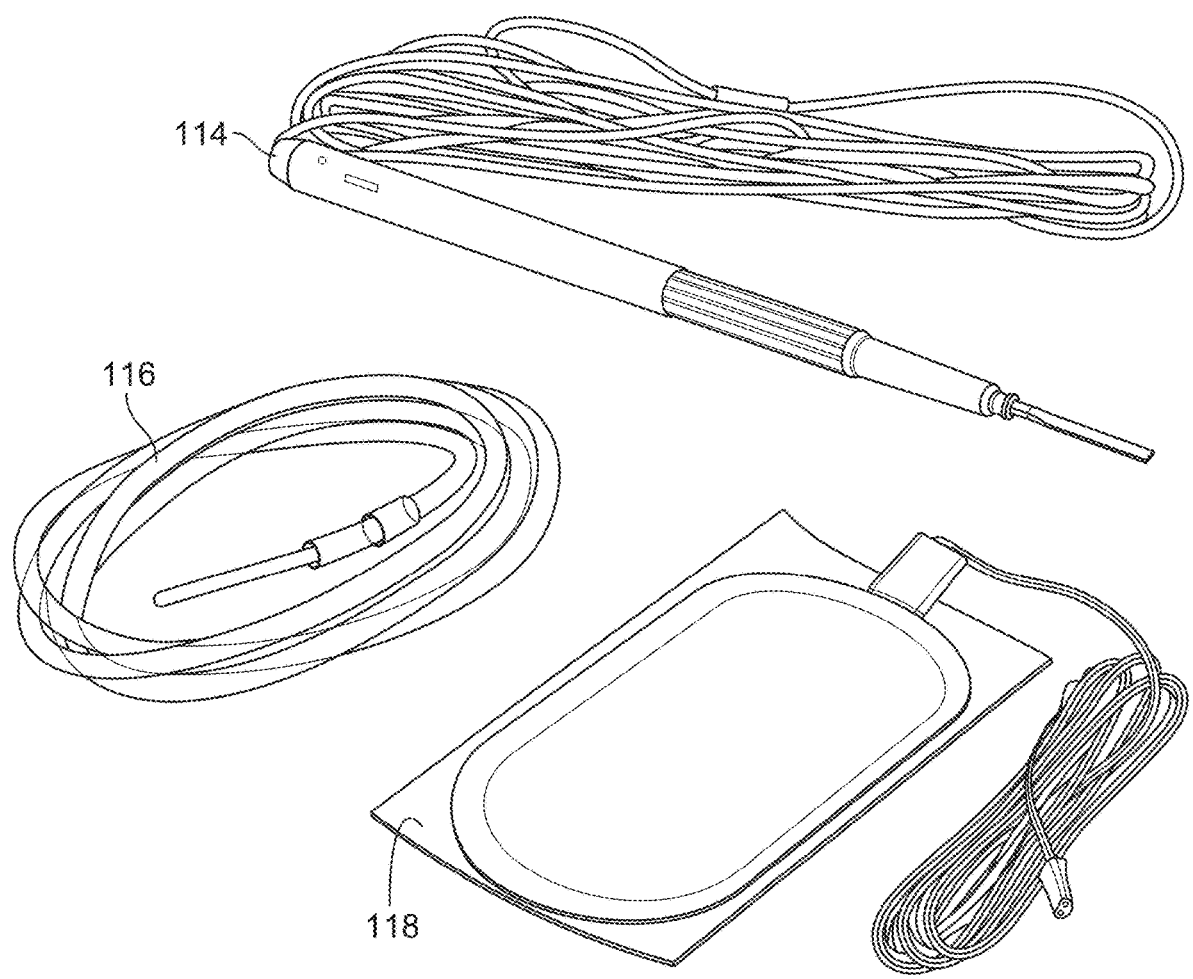
FIG. 1B is an illustration of detachable components of an electrosurgery system.

Referring to FIGS. 1A and 1B, an electrosurgery system 100 can be used for a variety of surgical operations in which a high frequency (e.g., radio frequency) electrical current is generated to cut, coagulate, desiccate, fulgurate, etc. biological tissue. An electrosurgery system 100 can include a high frequency (HF) generator 102, an operating instrument 114, and a patient pad 118. The operating instrument 114 and the patient pad 118 can be plugged into the HF generator 102 at a port interface 112 to be electrically connected to the HF generator 102. In some cases, operating instrument 114 is a monopolar instrument, receiving an active output from the HF generator 102, with the tip of the operating instrument serving as the active electrode of the electrosurgery system 100. In cases where a monopolar instrument is used, the patient pad 118 can serve as a dispersive electrode (also referred to as a ground pad or return electrode) of the electrosurgery system 100. In some cases, the patient pad 118 comprises a metal plate or a flexible metalized plastic pad. In some cases, the patient pad 118 can have a "split pad" configuration including two or more metal plates and/or flexible metalized plastic pads.

During a surgical operation using the electrosurgery system 100, the operating instrument 114 is used by an operator (e.g., a surgeon) to make contact with a patient's biological tissue at the site of operation, while the patient pad 118 is kept in direct contact with the patient at a site that is separate from the site of operation. The HF generator 102 generates a high frequency (e.g., 400 kHz to 600 kHz), alternative polarity electrical current, which oscillates between the operating instrument 114 and the patient pad 118, travelling through the patient's body. The patient pad 118 disperses the electrical current to prevent thermal injury to the patient.

The HF generator 102 may have one or more of the following features. In some cases, the HF generator 102 includes a control interface 110 for controlling the output generated by the HF generator. For example, the control interface 110 may include a display to show an operator the level of power being generated. The control interface 110 may also include buttons for raising or lowering the power output of the HF generator 102. In some cases, the control interface 110 can have buttons corresponding to predetermined outputs for specific operations such as cutting or coagulating biological tissue.

The HF generator 102 can also include a display interface 108 for providing information to an operator. For example, the display interface 108 can include LED indicators that light up to alert an operator when the patient pad 118 is loose or disconnected, when there is current leakage, when the electrosurgery system 100 is ready, when current is being generated, etc.

The HF generator 102 can further include a foot switch port 120, through which a foot switch can be connected to the HF generator 102, allowing an operator to control the output of the HF generator 102 with his/her feet if his/her hands are occupied.

In addition to the HF generator 102, the operating instrument 114, and the patient pad 118, the electrosurgery system 100 can include one or more of the following components. The electrosurgery system 100 can include a stand 104, which can support the HF generator 102, and can be adapted to facilitate safe and easy mobility of the electrosurgery system 100 around an operating room. The electrosurgery system 100 can also include a smoke evacuator 106, configured to vacuum byproducts and eliminate odors at the site of operation. In some cases, the smoke evacuator 106 can be attached to or located at the stand 104, which may be separate from the site of operation. In such cases, smoke evacuator tubing 116 can be used to provide suction at the site of operation, while providing connection to the remotely located smoke evacuator 106.

Figure 2:
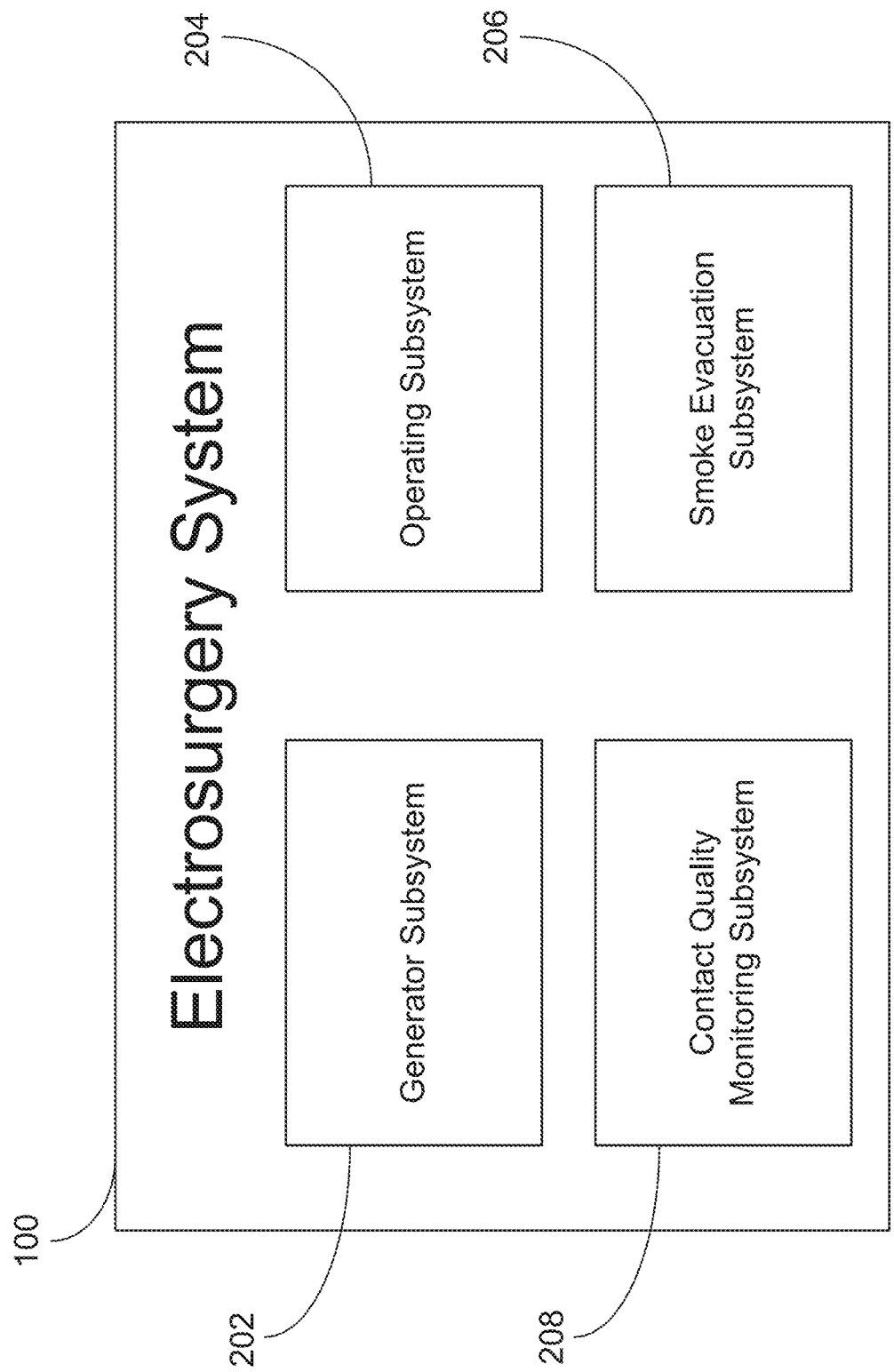
FIG. 2 is a functional block diagram of an electrosurgery system.

Referring to FIG. 2, the electrosurgery system 100 can contain a plurality of functional subsystems. These subsystems can include a generator subsystem 202, an operating subsystem 204, a smoke evacuation subsystem 206, and a contact quality monitoring subsystem 208, among other things.

The generator subsystem 202 of the electrosurgery system 100 includes the HF generator 102 and is responsible for generating the electrical current that is used for cutting, coagulating desiccating, or fulgurating, etc. the biological tissue.

The operating subsystem 204 of the electrosurgery system 100 provides direct contact with the patient as well as control for the operator throughout the surgical procedures. The operating system 204 of the electrosurgery system 100 includes the operating instrument 114, the patient pad 118, and the control interface 110 of the HF generator 102.

The smoke evacuation subsystem 206 of the electrosurgery system provides suction at the site of operation to vacuum byproducts and eliminate odors. The smoke evacuation subsystem includes smoke evacuator 106 and smoke evacuator tubing 116.

The contact quality monitoring subsystem 208 ensures that consistent and direct contact is made between the patient and the patient pad, and alerts the operator when contact is not being made. Due to the potentially dangerous levels of current generated by the generator subsystem and passing through the patient, monitoring of this contact is needed in order to prevent thermal injury to the patient. The contact quality monitoring subsystem 208 can be physically embodied by the circuitry within the HF generator 102, which is described in further detail herein.

Figure 3:
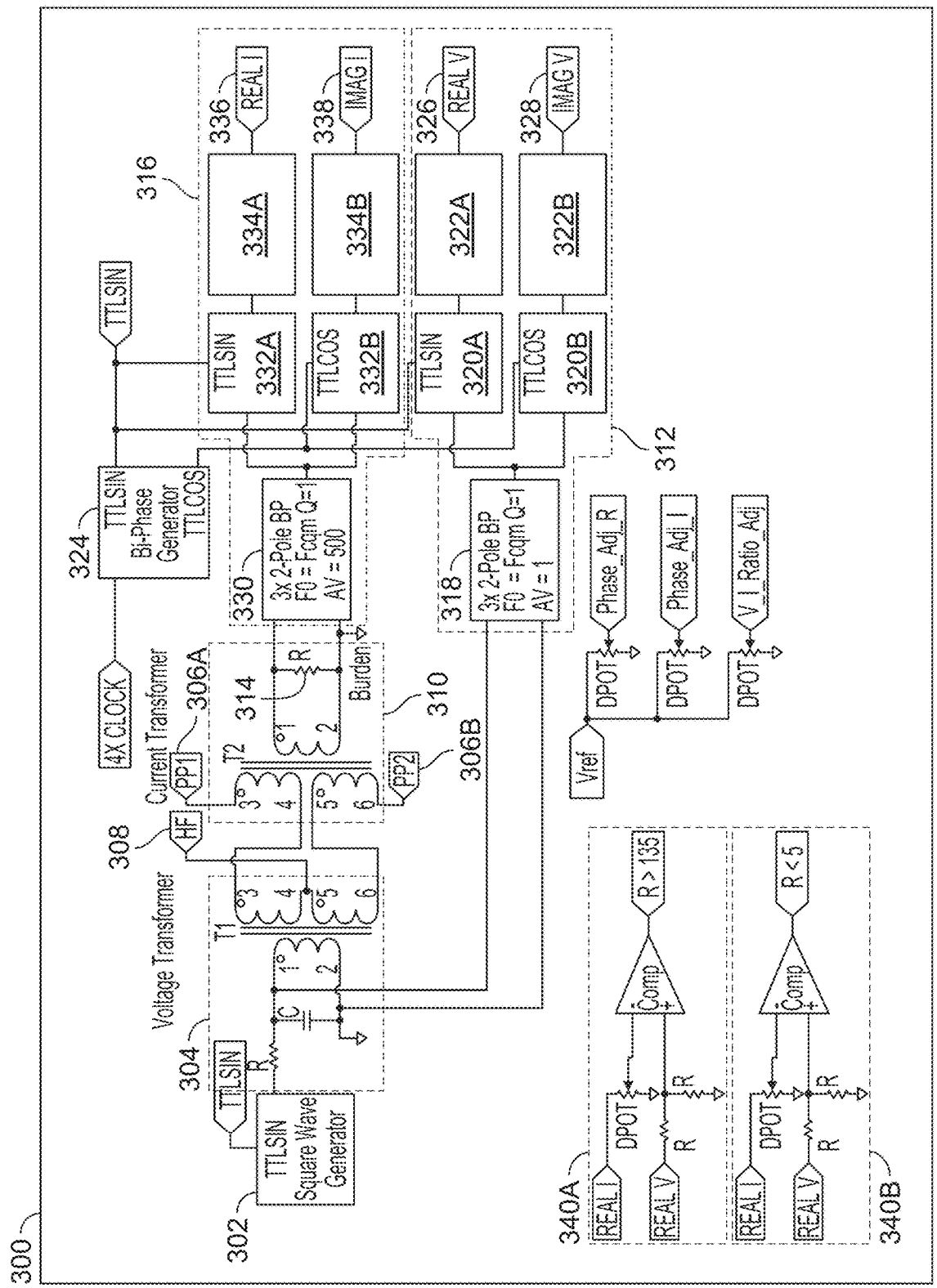
FIG. 3 is a circuit diagram of an electrosurgery patient pad monitoring circuit.

FIG. 3 presents one arrangement of a patient pad monitoring circuit 300 used for monitoring the contact quality between a patient and the patient pad 118. The monitoring circuit 300 includes a square wave generator 302, which generates a measuring signal. The measuring signal applies a voltage to the split halves 306A, 306B of a patient pad (e.g., the patient pad 118 shown in FIG. 1) through a resonant transformer, referred to herein as a voltage transformer 304. The voltage transformer 304 has one primary and two secondary windings, however, other designed may be employed. For example, the voltage transformer 304 may include a single center-tapped secondary winding or other types of transformer designs. A signal representative of the excitation voltage is collected at the primary of the voltage transformer 304, and is passed through a voltage channel 312, which filters the signal and calculates a complex voltage associated with the signal.

The voltage channel 312 includes a 6-pole bandpass filter (3×2-pole filters) 318, which can amplify the voltage at the frequency of the measuring signal, while filtering signals at other frequencies (e.g., harmonics) and reducing interference from the HF signal 308 from the HF generator 102. Alternatively, the bandpass filter 318 can be implemented using other types of filters, e.g., 2×2-pole filters for a 4-pole bandpass filter. Following the bandpass filter 318, the resulting signal is fed to a pair of synchronous demodulators 320A, 320B, each of which converts the AC voltage to a DC voltage. The two synchronous demodulators receive different reference signals generated by a bi-phase generator 324, and the reference signals are 90 degrees out of phase, allowing for independent measurement of the real and imaginary components of the excitation voltage. The synchronous nature of the demodulators 320A, 320B also allows for measurement of the frequency of the measuring signal while rejecting most of the HF signal 308. The pair of synchronous demodulators 320A, 320B are each followed by a 4-pole low pass filter (2×2-pole filters) 322A, 322B, which reduces ripple generated by the demodulators 320A, 320B as well as ripple created by beat frequencies generated by interference between the measuring signal and the HF signal 308. The outputs from the voltage channel 312 represent the real (REALV 326) and the imaginary (IMAGV 328) components of the complex voltage.

On the secondary side of the voltage transformer 304, the measuring signal travels through a resonating circuit, and a second transformer, referred to herein as a current transformer 310, that enables the measurement of the current induced in the load by the voltage transformer 304. The current transformer has two primary windings and one secondary winding. Each primary is associated with one of the split halves 306A, 306B of the patient pad 118, and on the secondary side of the current transformer 310, a burden resistor 314 is connected in parallel with the secondary of the current transformer 310. The voltage generated across the burden resistor 314 is proportional to the sum of the current in the two primaries of the current transformer 310. This configuration provides high-resolution detail about the contact quality of the patient pad. For example, the circuit is able to measure the contact quality regardless of current path between the patient and the return electrode. A signal representative of the voltage across the burden resistor 314 is collected and is passed through a current channel 316, which filters the signal and calculates a complex current associated with the signal.

Similar to the voltage channel 312, the current channel 316 includes a 6-pole bandpass filter (3×2-pole filters) 330, which amplifies the voltage across the burden resistor 314 at the frequency of the measuring signal, while filtering signals at other frequencies (e.g., harmonics) and reducing interference caused by the HF signal 308 from the HF generator 102. Alternatively, the bandpass filter 330 can be implemented using one or more other filters (e.g., 2×2-pole filters for a 4-pole bandpass filter). Following the bandpass filter 330, the resulting signal is received by a pair of synchronous demodulators 332A, 332B, each of which converts the AC voltage to a DC voltage. The two synchronous demodulators 332A, 332B are fed with different reference signals generated by the bi-phase generator 324, and the reference signals are 90 degrees out of phase, allowing for independent measurement of the real and imaginary components of the current. In some cases, the reference signals received by the synchronous demodulators 332A, 332B in the current channel 316 are identical to those received by the synchronous demodulators 320A, 320B in the voltage channel 312. The synchronous nature of the demodulators 332A, 332B also allows for measurement of the frequency of the measuring signal without substantial interference from the HF signal 308. The pair of synchronous demodulators 332A, 332B are each followed by a 4-pole low pass filter (2×2-pole filters) 334A, 334B, which reduces ripple generated by the demodulators 332A, 332B as well as ripple created by beat frequencies generated by interference between the measuring signal and the HF signal 308. The outputs from the current channel 316 include real (REALI 336) and imaginary (IMAGI 338) components of the complex current.

The impedance of the patient pad 118 can be calculated from the outputs of the voltage channel 312 and the current channel 316. Calculation of the impedance can be performed by a computing device such as a microcontroller, which may be included in the HF generator 102. In some cases, the computing device may be an external device. To calculate impedance, the complex voltage is divided by the complex current as follows:

$$\text{Voltage} = \text{REALV} + i^*\text{IMAGV} \tag{1}$$

$$\text{Current} = \text{REAL } I + i^*\text{IMAGI} \tag{2}$$

$$\text{Impedance} = \text{Voltage}/\text{Current} \tag{3}$$

The real part of the complex impedance represents the measured resistance, and the imaginary part of the complex impedance represents the capacitive or inductive reactance.

In some arrangements, the performance of the patient pad monitoring circuit 300 may be improved by employing digital potentiometers (DPOTs) to calibrate for imperfections in the components of the circuit. For example, a second set of measurements can be performed without the benefit of the computing device. In auxiliary circuits 340A and 340B, output signals (REALI 336) and (REALV 326) are provided to a comparator, a fraction of each voltage is compared to the other, and the fraction may be adjusted by a DPOT. In this example, the auxiliary circuit 340A detects when the resistance exceeds 135Ω, and the auxiliary circuit 340B detects when then resistance is less than 5Ω.

If the measured resistance of the patient pad 118 is outside of an acceptable range, (e.g. 5Ω to 135Ω), the contact quality monitoring subsystem 208 of the electrosurgery system 100 can alert an operator that the patient is not making direct and/or consistent contact with the patient pad. For example, an LED indicator on the display interface 108 of the HF generator 102 can be turned on to indicate that the patient pad is loose. Resistance within a range of 0Ω to 5Ω can be measured for a single pad while a measurement between 5Ω to 135Ω can be considered a reasonable reading for a split pad design. Measurements above 135Ω can be considered as being indicative of a bad connection. In addition to visual indicators, audio indicators may be generated such as an alarm. Alternatively, or in addition, in response to identifying that the measured resistance of the patient pad 118 is outside of an acceptable range, the contact quality monitoring subsystem 208 can disable the generator subsystem 202 of the electrosurgery system 100 so that the HF generator cannot generate any potentially hazardous electrical current.

Figure 4:
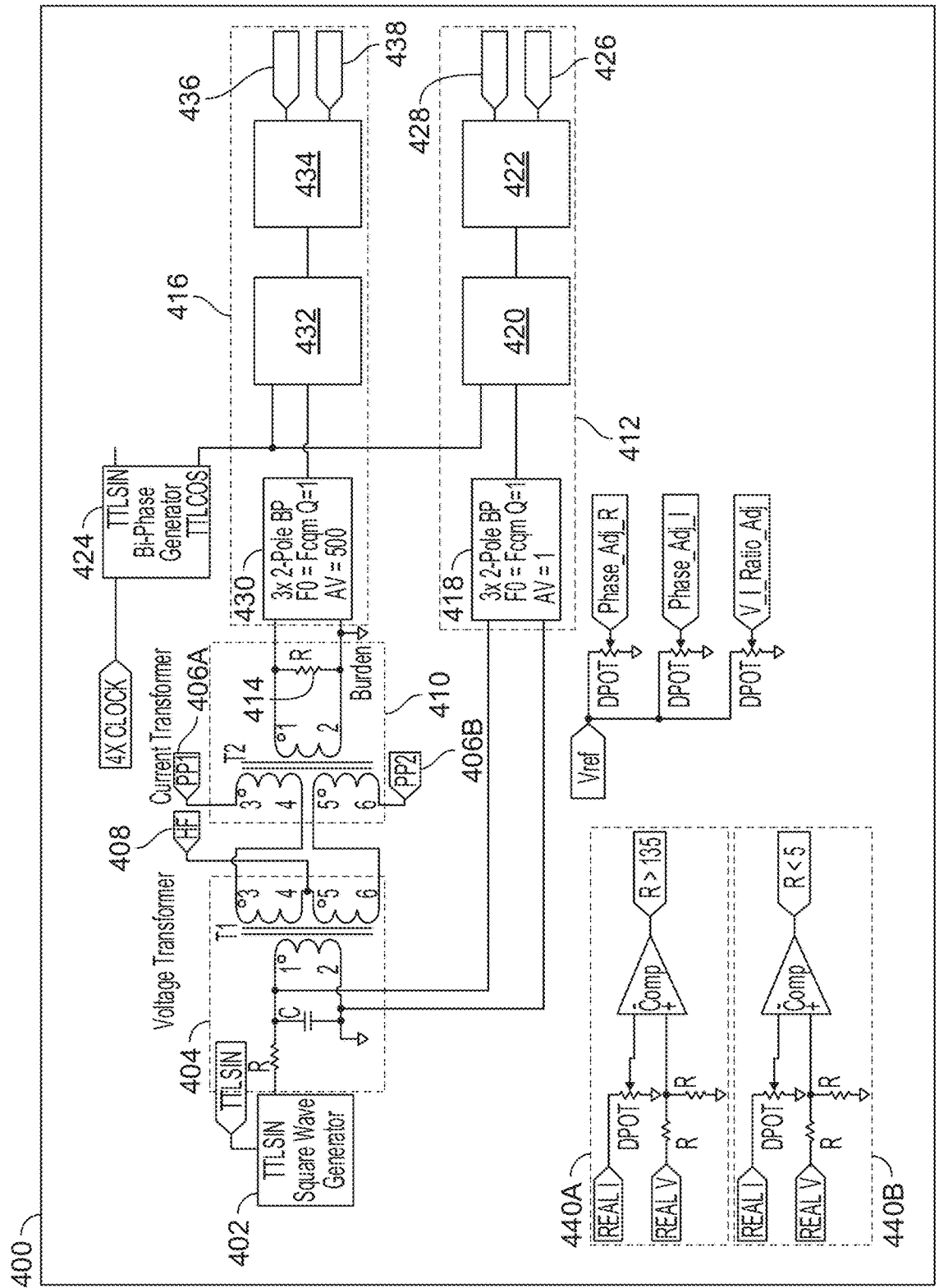
FIG. 4 is a circuit diagram of an electrosurgery patient pad monitoring circuit with a reduced component set.

FIG. 4 presents another implementation of a patient pad monitoring circuit 400 with a reduced component set. While the patient pad monitoring circuit 300 of FIG. 3 performs real and imaginary measurements simultaneously, the circuit 400 presented in FIG. 4 performs these measurements in sequence. In this implementation, the patient pad monitoring circuit 400 includes two single phase generators 424 and 402. The phase difference between these two generators 424, 402 can be programmed by a computational device (e.g., a microcontroller). The phase difference between the two generators 424, 402 is not limited to 90 degrees, but can be set with high resolution. Referring briefly to FIG. 3 (with FIG. 4), while the bi-phase generator 324 simultaneously outputs two reference waves, 90 degrees out of phase, the single phase generator 424 sequentially changes the phase of the output. In this arrangement, a voltage channel 412 requires only one synchronous demodulator 420 and one 4-pole low pass filter 422. Similarly, a current channel 416 requires only one synchronous demodulator 432 and one 4-pole low pass filter 434. In one implementation, the synchronous demodulators 420, 432 each includes an inverting amplifier so that each signal is available in positive and negative polarities (i.e., 180 degrees out of phase) and is alternatively switched by the reference signal output by the single phase generator 424 at the same frequency as that of the measuring signal. By obviating the need for a second synchronous demodulator and low-pass filter for each of the voltage channel 312 and the current channel 316, the patient pad monitoring circuit 400 employs fewer components, thereby reducing real estate needs, power consumption, costs, etc.

Both patient pad monitoring circuit 300 and patient pad monitoring circuit 400 enable accurate and reliable impedance measurements of the patient pad 118. For example, both monitoring circuits 300, 400 are robust to parallel resistances that may exist in the voltage transformers 304, 404 and the current transformers 310, 410. While a parallel resistance in the voltage transformer 304, 404 can affect the level of the excitation voltage, measuring the resulting voltage across the primary of the voltage transformer 304, 404 enables the monitoring circuits 300, 400 to account for that effect. Similarly, while a parallel resistance may be present in the current transformer 310, 410, measuring the resulting voltage across the burden resistor 314, 414 of the current transformer 310, 410 enables the monitoring circuits 300, 400 to account for its effect.

Moreover, the configuration of patient pad monitoring circuit 300 and patient pad monitoring circuit 400 enables a technique for preventing undesired interference between the measuring signal and the HF signal 308, 408 generated by the HF generator 102 while ensuring resonance of the voltage transformer 304, 404. In an example, the HF generator 102 of the electrosurgery system 100 operates at 495 kHz, up to about 4000V, and up to 1.5 A—2 A. This can generate significant amounts of interference with the measuring signal depending on the frequency of the measuring signal. Thus, it is desirable to select a frequency of the measuring signal that limits interference with the HF signal 308, 408 without the need to adjust the frequency of the measuring signal. In some cases, a coagulation signal of the electrosurgery system 100 is a high voltage, short duty cycle signal comprising 2 cycles at 495 kHz and 30 cycles of nothing. Consequently, sidebands appear at every ~15.5 kHz (495 kHz/32 cycles) due to harmonics. Therefore, in this example, a frequency of the measuring signal should be selected so that its multiples (i.e., harmonics) do not create beat frequencies with the 15 kHz harmonics around 495 kHz. An example frequency for the measuring signal that meets this requirement is 137 kHz, although other frequencies may also be chosen.

Once a frequency for the measurement signal is selected, it is still important to ensure that it is at the right frequency for resonance of the voltage transformer 304, 404. Since the measuring frequency has already been selected and is fixed, the patient pad monitoring circuits 300, 400 can be designed to have a low Q factor (e.g., 3 to 40), allowing for broad resonance and ensuring that transformer resonance is achieved. Furthermore, to address the issue of phase shift, the bi-phase generator 324 or the single phase generator 424 can be adjusted so that the imaginary components calculated by the voltage channel 312, 412, and the current channel 316, 416 are both 0.

Figure 5:
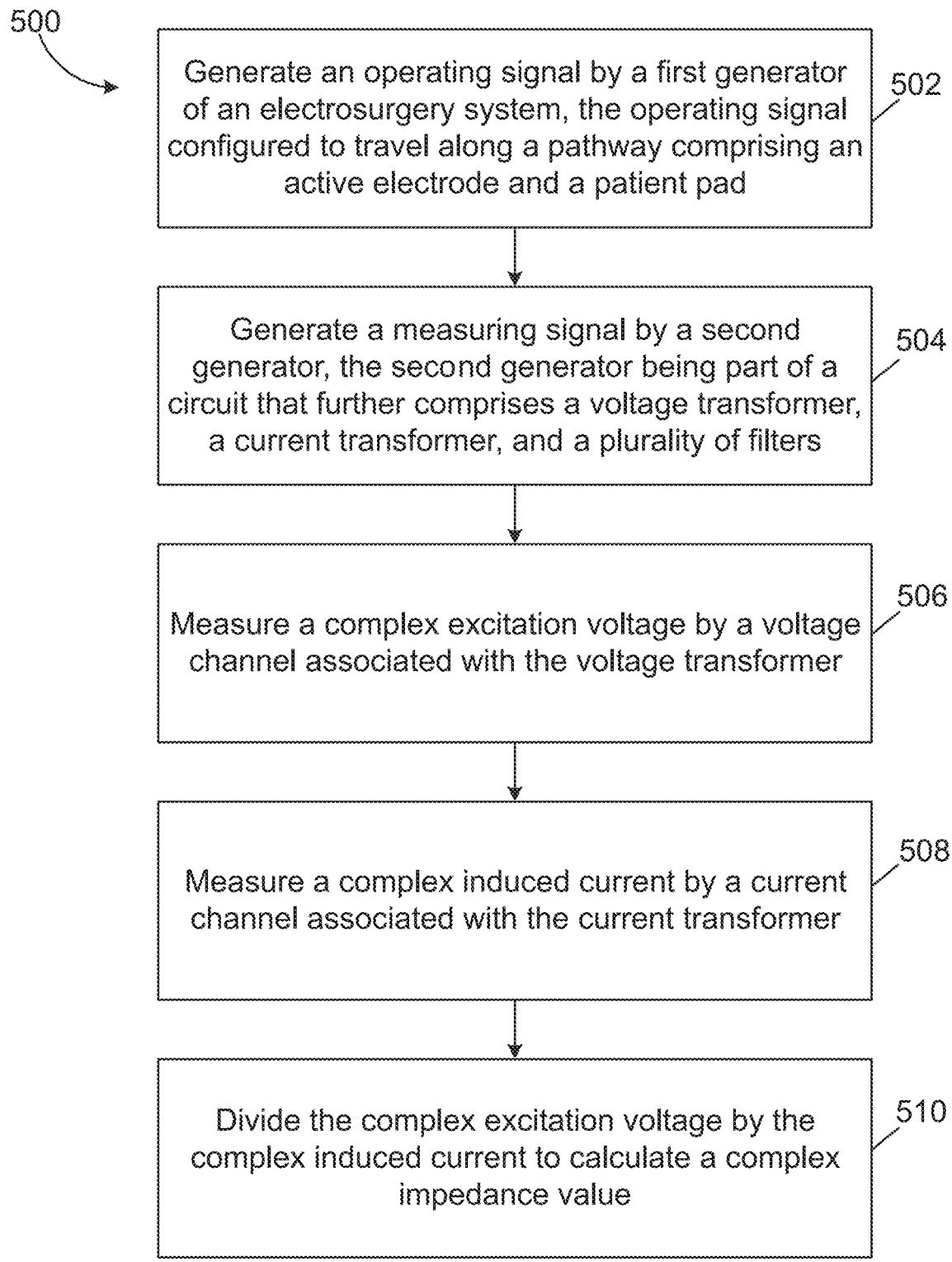
FIG. 5 is a flow chart of a complex impedance measurement process for an electrosurgery system.

FIG. 5 is a flowchart 500 that presents operations for monitoring the complex impedance of a patient pad. Operations include, generating an operating signal 502 by a first generator of an electrosurgery system, the operating signal configured to travel along a pathway comprising an active electrode and a patient pad. For example, the operating signal can be the HF signal 308 generated by the HF generator 102 of the electrosurgery system 100, and the active electrode can correspond to the operating instrument 114. Operations also include, generating a measuring signal 504 by a second generator, the second generator being part of a circuit that further comprises a voltage transformer, a current transformer, and a plurality of filters. The circuit can be a patient pad monitoring circuits such as patient pad monitoring circuits 300, 400. The voltage transformer can correspond to the voltage transformers 304, 404 of patient pad monitoring circuits 300, 400. The current transformer can correspond to the current transformers 310, 410 of patient pad monitoring circuits 300, 400. The plurality of filters can correspond to the bandpass filters 318, 330, 418, 430 and the low pass filters 322A-B, 334A-B, 422, 434 of patient pad monitoring circuits 300, 400.

A complex excitation voltage is measured 506 by a voltage channel associated with the voltage transformer. The complex excitation voltage can have real and imaginary components such as REALV 326, 426 and IMAGV 328, 428 respectively. The voltage channel can correspond to the voltage channel 312, 412 of patient pad monitoring circuits 300, 400. Similarly, a complex induced current is measured 508 by a current channel associated with the current transformer. The complex induced current can have real and imaginary components such as REALI 336, 436 and IMAGI 338, 438 respectively. The current channel can correspond to the current channel 316, 416 of patient pad monitoring circuits 300, 400. Operations further include dividing 510 the complex excitation voltage by the complex induced current to calculate a complex impedance value. The complex impedance value can have a real component corresponding the resistance of a patient pad 118 and a complex component corresponding to the capacitive or inductive reactance of the patient pad monitoring circuits 300, 400.

Figure 6:
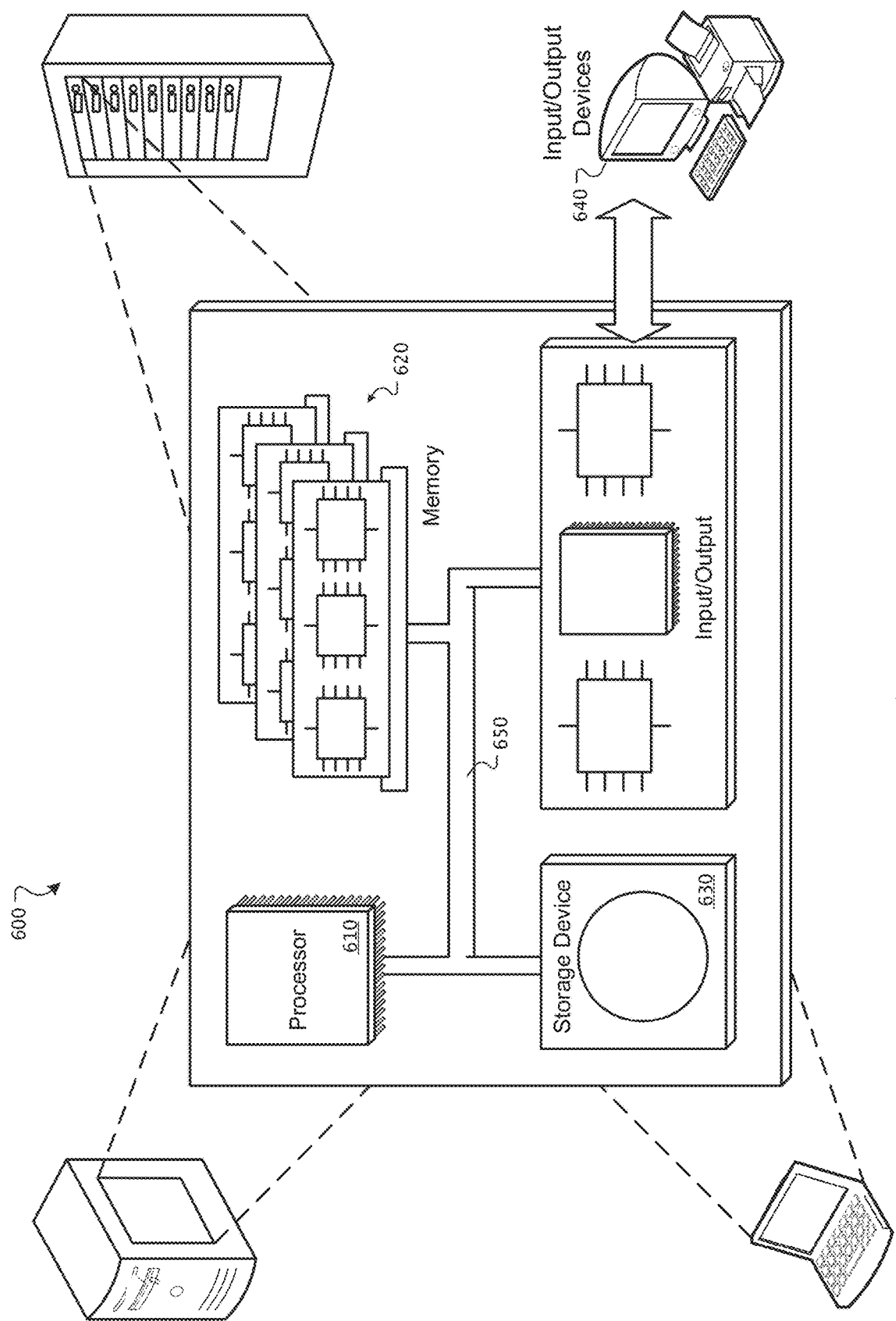
FIG. 6 shows an example of a computer device and a mobile computer device, which may be used with the techniques described here.

FIG. 6 is a schematic diagram of a generic computer system 600. The system 600 can be used for the operations described in association with any of the computer-implemented methods described previously, according to one implementation. The system 600 includes a processor 610, a memory 620, a storage device 630, and an input/output device 640. Each of the components 610, 620, 630, and 640 are interconnected using a system bus 650. The processor 610 is capable of processing instructions for execution within the system 600. In one implementation, the processor 610 is a single-threaded processor. In another implementation, the processor 610 is a multi-threaded processor. The processor 610 is capable of processing instructions stored in the memory 620 or on the storage device 630 to display graphical information for a user interface on the input/output device 640.

The memory 620 stores information within the system 600. In some implementations, the memory 620 is a computer-readable medium. The memory 620 is a volatile memory unit in some implementations and is a non-volatile memory unit in other implementations.

The storage device 630 is capable of providing mass storage for the system 600. In one implementation, the storage device 630 is a computer-readable medium. In various different implementations, the storage device 630 may be a floppy disk device, a hard disk device, an optical disk device, or a tape device.

The input/output device 640 provides input/output operations for the system 600. In one implementation, the input/output device 640 includes a keyboard and/or pointing device. In another implementation, the input/output device 640 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

The patient pad monitoring circuit 400 (shown in FIG. 4) can be capable of providing other functionality; for example, self-calibration can be performed. One or more techniques may be used for calibration, for example, references points (e.g., three points) may be provided for expected measured impedances. In one arrangement, the three points represent a short circuit condition, a fixed resistance value condition (e.g., a 135Ω measurement), and an open-circuit condition. The short circuit condition is a minimal impedance condition experienced by the circuit, thereby enabling the circuit to calibrate at a low level (e.g., at its electrical noise floor). The fixed resistance condition (e.g., 135Ω) measurement allows the circuit 400 to self-calibrate at the tripping frequency, and the open circuit condition allows the circuit to recognize the generation of a maximum possible signal.

A number of embodiments have been described. Nevertheless, it will be understood that various modifications can be made without departing from the spirit and scope of the processes and techniques described herein. In addition, the logic flows depicted in the figures do not require the particular order shown, or sequential order, to achieve desirable results. In addition, other steps can be provided, or steps can be eliminated, from the described flows, and other components can be added to, or removed from, the described systems. Accordingly, other embodiments are within the scope of the following claims.

What is claimed is:
1. An electrosurgery system comprising:
a patient pad; and
a circuit configured to measure an impedance of the patient pad, the circuit comprising:
 a voltage transformer configured to receive a measuring signal at a primary of the voltage transformer and configured to receive an operating signal at a secondary of the voltage transformer, the secondary of the voltage transformer being connected to the patient pad; and a current transformer connected, at a primary of the current transformer, to the secondary of the voltage transformer;

wherein a current induced in the patient pad by the secondary of the voltage transformer is measured, by the current transformer, based on connection of the primary of the current transformer to the secondary of the voltage transformer.

2. The electrosurgery system of claim 1, wherein the voltage transformer comprises a resonant transformer.

3. The electrosurgery system of claim 1, wherein the voltage transformer comprises:
one primary; and
two secondaries, or
a single center-tapped secondary.

4. The electrosurgery system of claim 1, wherein the current transformer comprises a first primary, a second primary, and one secondary.

5. The electrosurgery system of claim 4, wherein the secondary of the current transformer is configured to measure a sum of a first current corresponding to the first primary of the current transformer and a second current corresponding to the second primary of the current transformer.

6. The electrosurgery system of claim 1, wherein a frequency of the measuring signal is fixed.

7. The electrosurgery system of claim 6, wherein the frequency of the measuring signal is selected to prevent beat frequencies resulting from interference with the operating signal.

8. The electrosurgery system of claim 6, wherein the frequency of the measuring signal is selected to be within a range of 136 kHz to 138 kHz.

9. The electrosurgery system of claim 1, wherein the operating signal has a frequency within a range of 494 kHz to 496 KHz.

10. The electrosurgery system of claim 1, the circuit further comprising:
a voltage channel configured to measure an excitation voltage associated with the voltage transformer, and
a current channel configured to measure a induced current associated with the current transformer.

11. The electrosurgery system of claim 10, wherein the impedance is calculated by dividing the excitation voltage by the induced current.

12. The electrosurgery system of claim 10, wherein the voltage channel comprises:
a first set of bandpass filters,
a first synchronous demodulator, and
a first set of low pass filters; and
wherein the current channel comprises:
a second set of bandpass filters,
a second synchronous demodulator, and
a second set of low pass filters.

13. The electrosurgery system of claim 12, wherein the first synchronous demodulator is configured to sequentially receive a first reference signal and a second reference signal, a 90 degree phase difference is experienced by the first synchronous demodulator when the second reference signal is received relative to a phase difference experienced by the first synchronous demodulator when the first reference signal is received.

14. A method for monitoring an impedance of a patient pad, the method comprising:
generating an operating signal in a patient pad;
generating a measuring signal for determining an impedance value in the patient pad;
measuring an excitation voltage associated with a voltage transformer configured to receive the measuring signal at a primary of the voltage transformer and configured to receive the operating signal at a secondary of the voltage transformer, the secondary of the voltage transformer being connected to the patient pad;
measuring an induced current associated with a current transformer connected, at a primary of the current transformer, to the secondary of the voltage transformer, wherein the induced current is based on connection of the primary of the current transformer to the secondary of the voltage transformer; and
dividing the excitation voltage by the induced current to determine the impedance value in the patient pad.

15. The method of claim 14, wherein the voltage transformer comprises:
one primary; and
two secondaries, or
a single center-tapped secondary.

16. The method of claim 14, wherein the current transformer comprises two primaries and one secondary.

17. The method of claim 14, wherein the secondary of the current transformer is configured to measure a sum of a first current corresponding to a first primary of the current transformer and a second current corresponding to a second primary of the current transformer.

18. The method of claim 14, wherein a voltage channel, configured for measuring the excitation voltage, comprises:
a first set of bandpass filters,
a first synchronous demodulator, and
a first set of low pass filters; and
wherein a current channel, configured for measuring the induced current, comprises:
a second set of bandpass filters,
a second synchronous demodulator, and
a second set of low pass filters.

19. The method of claim 18, wherein the first synchronous demodulator is configured to sequentially receive a first reference signal and a second reference signal, a 90 degree phase difference is experienced by the first synchronous demodulator when the second reference signal is received relative to a phase difference experienced by the first synchronous demodulator when the first reference signal is received.

20. The method of claim 18, wherein each of an open circuit condition, a fixed resistance condition, and a short circuit condition are used for self-calibration.

* * * * *